United States Patent
Lee et al.

(10) Patent No.: US 9,408,918 B1
(45) Date of Patent: Aug. 9, 2016

(54) FRET-BASED MESOPOROUS SILICA NANOPARTICLES FOR REAL-TIME MONITORING OF DRUG RELEASE

(71) Applicant: Rutgers, The State University of New Jersey, New Brunswick, NJ (US)

(72) Inventors: Ki-Bum Lee, Monmouth Junction, NJ (US); Jinping Lai, Highland Park, NJ (US); Birju Shah, Piscataway, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 166 days.

(21) Appl. No.: 14/203,559

(22) Filed: Mar. 10, 2014

Related U.S. Application Data

(60) Provisional application No. 61/775,131, filed on Mar. 8, 2013.

(51) Int. Cl.
*A61K 47/00* (2006.01)
*A61K 47/40* (2006.01)
*A61K 47/02* (2006.01)

(52) U.S. Cl.
CPC ............... *A61K 47/40* (2013.01); *A61K 47/02* (2013.01)

(58) Field of Classification Search
CPC ............................ A61K 47/40; A61K 47/02
USPC ....................................................... 514/777
See application file for complete search history.

(56) References Cited

PUBLICATIONS

Lai et al, ACS Nano, 2013.*

\* cited by examiner

*Primary Examiner* — Jason Sims
*Assistant Examiner* — Ibrahim D Bori
(74) *Attorney, Agent, or Firm* — Fox Rothschild LLP

(57) ABSTRACT

A compound comprising: (a) a drug carrier comprising coumarin-labeled-cysteine tethered mesoporous silica nanoparticles (MSNs) loaded with a pharmaceutically active agent, and (b) a fluorescein isothiocyanate-β-cyclodextrin (FITC-β-CD) covalently linked to said cysteine and blocking the release of said pharmaceutically active agent from said nanoparticles, wherein cleavage of said covalent linkage removes said cyclodextrin and releases said pharmaceutically active agent, and said coumarin and said fluorescin form a donor-acceptor pair so that said drug carrier has a first emission wavelength when the covalent linkage is intact and the cyclodextrin said present and a second emission wavelength after cleavage of said covalent linkage to remove said cyclodextrin and release said pharmaceutically active agent.

15 Claims, 5 Drawing Sheets

FRET-BASED MESOPOROUS SILICA NANOPARTICLES FOR REAL-TIME MONITORING OF DRUG RELEASE

CROSS-REFERENCE TO RELATED APPLICATION

The present application claims priority benefit under 35 USC §119(e) to U.S. Provisional Application Ser. No. 61/775,131 filed Mar. 8, 2013, the disclosure of which is incorporated by reference herein in its entirety.

STATEMENT OF GOVERNMENT RESEARCH SUPPORT

This invention was made with government support under Director's Innovator Award 1DP20D006462-01 awarded by the National Institutes of Health. The government has certain rights in the invention.

BACKGROUND

It has been known that diseased/injured microenvironments release different biological cues and follow abnormal regulatory cycles, when compared to physiologically normal cells and tissues. Such dynamic microenvironmental conditions require scientists to develop more effective nanomaterial-based drug delivery systems (DDSs) having the following attributes: i) they can deliver multiple drugs such as organic small molecules, proteins, peptides, DNA, and RNAi molecules without any physicochemical alterations to drug structure, ii) they can modulate the drug-release profile in response to external or internal stimuli for enhancing therapeutic efficacy and minimizing side-effects of drug treatment, and iii) they can monitor the drug release in real time for investigating accumulation of the drugs at the targeted area.

In this regard, mesoporous silica nanoparticles (MSNs) have excellent potential as DDSs owing to their unique porous structure, tunable pore size, biocompatibility, ease of surface functionalization, and overall versatility. The hexagonal-ordered pore network within these MSNs allows for entrapping drugs within these pores by simple diffusion. Additionally, the pores can be functionalized with molecular valves designed to trigger the release of the entrapped drugs in the presence of external or internal stimuli including light, temperature, pH, and biomolecules. While there have been numerous reports on the design and development of stimuli-responsive MSNs for drug delivery, development of strategies for real-time monitoring of drug release inside the targeted cells is still in its nascent stage.

The most widely used amongst these strategies include using fluorescent dyes/drugs as a model cargo system, or conjugating the drugs with caged dyes. However, such strategies come with their own limitations such as difficulty in correlating the release of the fluorescent model dye to that of the actual drug molecules; restricting the usage of fluorescent drugs like doxorubicin as model cargoes, although most of the current drug candidates are non-fluorescent; and possibility of affecting the therapeutic efficacy of the drug owing to structural changes required for conjugation of dyes. Such challenges in investigating the release of drug in complex cellular microenvironments necessitate the development and integration of a real-time monitoring system within the stimuli-responsive nanomaterial-based DDSs.

SUMMARY OF THE INVENTION

To address the aforementioned issues, herein we describe the synthesis and development of a redox-responsive fluorescent resonance energy transfer based MSN drug delivery system (henceforth referred to as FRET-MSN), which enables real-time monitoring (based upon the FRET signal) of redox-responsive drug release occurring in the presence of glutathione found in significantly higher levels in the cancer cells. Fluorescence resonance energy transfer (or Förster resonance energy transfer, FRET) is a well-established energy transfer process between two fluorophores which is very sensitive to changes at nanometer-scale (typically less than 10 nm) in the donor-to-acceptor separation distance. This unique feature of FRET can potentially be an ideal tool to monitor delicate interactions between nanomaterial-based DDSs and external/internal stimuli.

DESCRIPTION OF THE DRAWINGS

FIG. 1A is an magnified representation of FIG. 1B, indicating the FRET system;

DESCRIPTION OF THE INVENTION

Figure 1:
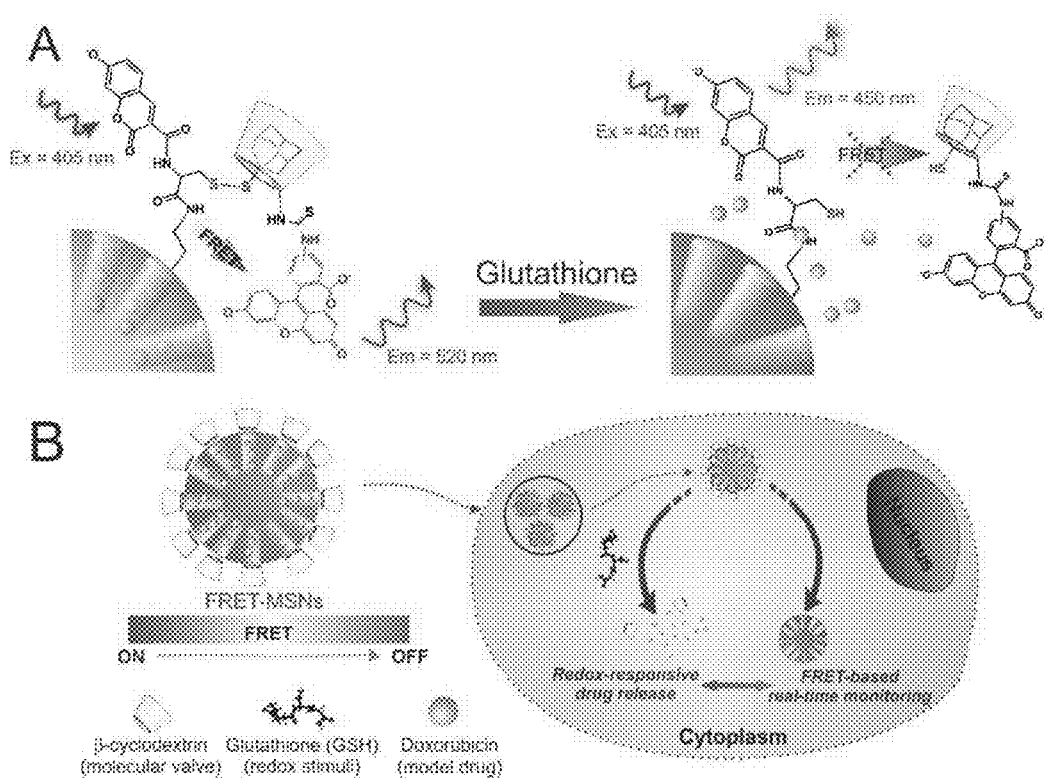
FIG. 1 depicts a schematic representation of the redox responsive FRET-MSNs. (A) The coumarin-labeled cysteine on the surface of the FRET-MSNs act as a donor and the FITC-$\beta$-CD act as an acceptor, thereby forming a FRET system when the disulfide bond is intact (left). When disulfide bond is cleaved in the presence of redox stimuli, glutathione, the FITC-$\beta$-CD, which also acts as the molecular valve, is removed from the surface of the MSNs, thereby the FRET between coumarin and FITC is abolished. (B) The delivery of encapsulated cargo is selectively triggered in the presence of the redox-stimuli, glutathione which is found in significantly higher amounts in the cytoplasm of cancer cells and the concomitant change of FRET signal can be used to report the uncaging event and estimate the dosing amount of drug.

As illustrated in FIG. 1, our FRET-based real-time monitoring platform is comprised of four components: i) coumarin (donor)-tethered MSNs as the drug carriers, (ii) fluorescein isothiocyanate (FITC, acceptor)-attached β-cyclodextrin (β-CD) as the molecular cap to entrap the drugs within the MSNs, (iii) disulfide linkage as the redox-responsive trigger to release the entrapped drug molecules, and (iv) FRET donor-acceptor pair of coumarin and FITC for monitoring drug release in real time. Under non-reducing conditions (e.g. without glutathione), the intact disulfide bond supports formation of a donor-acceptor complex between the coumarin-attached MSN and the FITC-β-CD molecular cap, thereby creating a FRET system. At this stage (FRET ON), the coumarin and FITC moieties are in close proximity on the MSN surface and the FRET-MSNs display an emission peak at 520 nm (correlated to energy transfer from coumarin to FITC), when they are excited at 405 nm (the excitation wavelength of coumarin).

However, in the presence of a reducing environment (e.g. with glutathione), the disulfide bond can be cleaved, causing the removal of the FITC-β-CD cap from the MSNs, thereby unlocking the pores and releasing the cargo within. Upon cleavage of the disulfide bond, the FITC-β-CD diffuses away from the MSN surface, hence the FRET between coumarin and FITC is abolished (FRET OFF), and the MSNs display emission at 450 nm (characteristic of coumarin) when excited at 405 nm. Since the on/off change in FRET signal is regulated by molecular structures within our platform and correlated to the unlocking event, we can monitor and quantify the drug release process, by measuring the change of FRET signal. By monitoring the FRET signal on the nanoparticles in real-time, we can visualize the release of any drug molecules, without relying on the drug's optical properties, thereby extending the application of our FRET-MSNs to many drug molecules without compromising their efficacy.

Synthesis and Characterization of FRET-MSNs.

Figure 2:
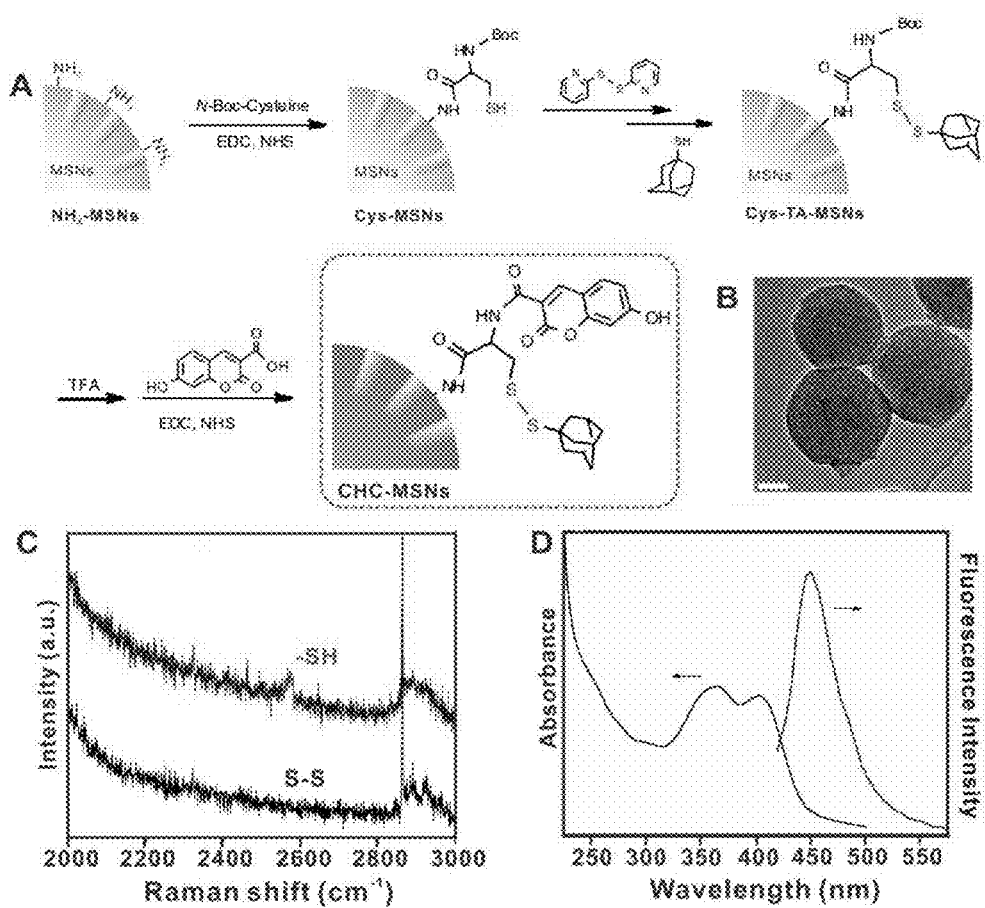
FIG. 2 depicts (A) Schematic illustration of the synthesis of CHC-labeled MSNs. The CHC moiety acts as the FRET donor in our FRET-MSNs. (B) TEM image of CHC-MSNs. Scale bar is 50 μm. TEM image confirms that CHC-MSNs retain characteristics typical of MCM-41 type nanoparticles. (C) Raman spectra confirming the formation of a disulfide bond, following conjugation with 1-adamantane thiol. The top curve indicates the free thiol (—SH) moiety on the surface of CHC MSNs, prior to conjugation with 1-adamantane thiol. Following conjugation, no free —SH groups are observed as shown in the bottom curve, thus indicating successful formation of disulfide bond. (D) U-V absorbance and emission spectra for CHC-MSNs. The CHC moiety in the CHC-MSNs absorbs maximally at 405 nm and emits light corresponding to 450 nm, thereby acting as a FRET donor for FITC.

The generation of our FRET-MSN-based drug delivery system began with the synthesis of MCM-41type MSNs via condensation of tetraethylorthosilicate (TEOS) in the presence of a cetyltrimethylammonium bromide (CTAB) micelle template (FIG. 2A). These MSNs were then functionalized with 3-aminopropyltriethoxysilane (APTES) and grafted with N-Boc-cysteine via an amide bond. The thiol group of cysteine was conjugated with 1-adamantanethiol to form an redox-responsive disulfide bond, while the amine group was further labeled with 3-carboxy-7-hydroxyl-coumarin (CHC) to obtain the functional CHC-MSNs.

Using transmission electron microscopy (TEM), we affirmed that the CHC-MSNs still retain the characteristics of MCM-41 type of MSNs, such as their spherical particle shape, having an average diameter of 100 nm±14 nm (n=100) and hexagonally packed mesoporous structures (FIG. 2B). This was also substantiated by $N_2$ adsorption isotherms which demonstrated that the CHC-MSNs have a Burnauer-Emmett-Teller (BET)-surface area of 398 $m^2·g^{-1}$ and a narrow Barrett-Joyner-Halenda (BJH) pore-size distribution (average pore diameter=2.3 nm.

In addition, the cysteine functionalized MSNs show a characteristic Raman peak of free thiol group at 2550 $cm^{-1}$ (FIG. 2C, top curve). However, after conjugation with 1-adamantanethiol via a disulfide bond, this characteristic free thiol peak disappeared, which confirmed the formation of a disulfide bond (FIG. 2C bottom curve). FIG. 2D shows the UV-Vis absorption and fluorescence emission of CHC-MSNs, demonstrating the successful conjugation of CHC to the MSN surface and indicates that the CHC-moiety can act as the energy donor for FITC. Together with FTIR characterization of CHC-MSNs, these results demonstrated the successful construction of CHC-MSNs.

Assembly of a Donor-Acceptor FRET Model.

Figure 3:
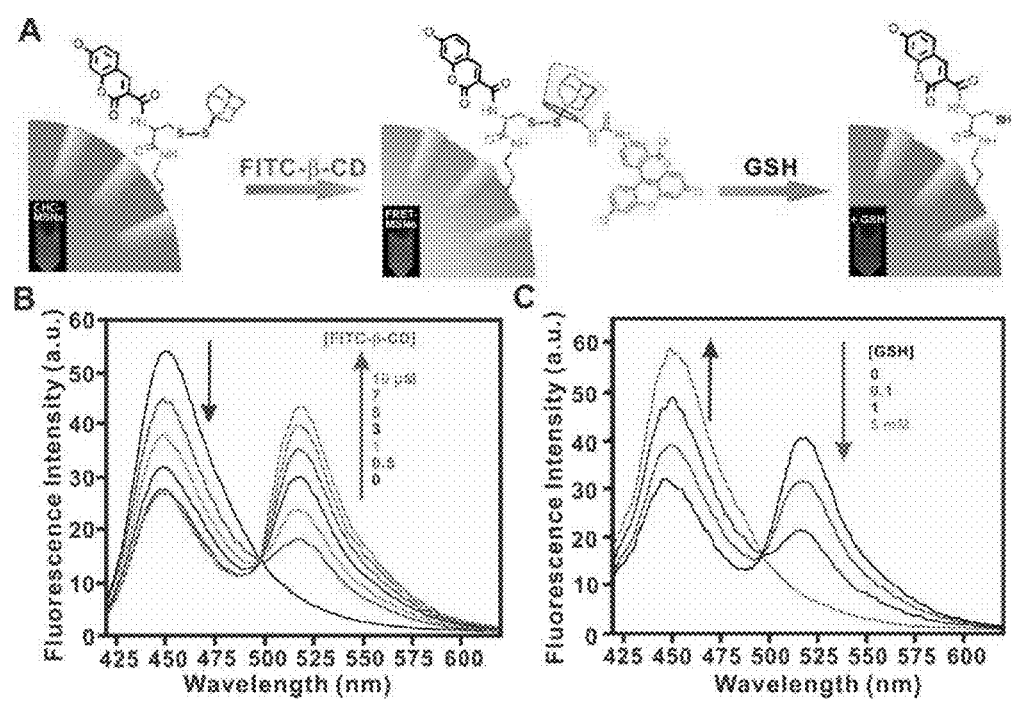
FIG. 3 depicts (A) Schematic diagram indicating the assembly of FRET MSNs (left), upon addition of FITC-$\beta$-CD to CHC-MSNs; and subsequent cleavage of disulfide bond (right), following treatment of FRET-MSNs with Glutathione (GSH). Inset figures show the corresponding change in color of the nanoparticle solution under UV lamp (365 nm). (B) Changes in blue (450 nm) and green (520 nm) fluorescence upon addition of increasing concentrations of FITC-$\beta$-CD to the CHC-MSNs dispersed in pH7.4 PBS, indicating formation of FRET-MSNs (FRET ON). (C) Changes in blue (450 nm) and green (520 nm) fluorescence upon addition of increasing GSH concentrations to FRET-MSNs dispersed in pH7.4 PBS, indicating cleavage of disulfide bond (FRET OFF)

The synthesis of FRET-MSNs was then followed by the combination of the CHC-MSNs with FITC-β-CD via host-guest complexation between FITC-β-CD and adamantane moiety present on CHC-MSNs (FIG. 3A). As shown in FIG. 2D, the coumarin moiety in CHC-MSNs can be excited by absorbing light with a wavelength of 405 nm, resulting in emission of light in the range of 430-480 nm. When the disulfide bond is intact (FIG. 1), the coumarin moiety in CHC-MSNs upon excitation at 405 nm will act as a photon donor for the FITC-β-CD which absorbs maximally at 480 nm.

We observed that the addition of FITC-β-CD lead to a decrease in blue fluorescence (450 nm) and an increase in green fluorescence (520 nm) (FIG. 3B), which was also reflected in a significant change of the color of the solution from blue to green, sufficiently distinct to be identified via naked eye (FIG. 3A, inset). As seen in FIG. 3B, further increases in the concentration of FITC-β-CD quenched the blue fluorescence maximally. Additionally, from the data shown in FIG. 3B, the ratio of relative fluorescence intensities (FRET signal R, where $R=F_{520\,nm}/F_{450\,nm}$) reached a value of 1.25 at a concentration of 3 µM for FITC-β-CD for a fixed concentration of CHC MSNs (10 µg·$mL^{-1}$), which indicated the assembly of FITC-β-CD to the MSN surface reached a saturation point.

Further addition of FITC-β-CD beyond the saturation point only led to an increase in the FITC fluorescence with negligible quenching of coumarin fluorescence, presumably due to the direct excitation of FITC at 405 nm. When these nanoparticles were isolated from the solution and redispersed in PBS (pH 7.4), they displayed dual emission peaks at 450 nm and 520 nm upon excitation at 405 nm. Collectively, these results demonstrated that FITC-β-CD can assemble onto the surface of the CHC-MSN surface through the formation of inclusion complex with 1-adamantanethiol, thereby inducing a donor-acceptor FRET system.

Redox-Responsive Behavior of FRET-MSNs.

The redox-responsive property of the FRET-MSNs was examined by observing the changes in FRET signal in the presence of glutathione (GSH) which mimics the intracellular reducing environment (FIG. 3A). As shown in FIG. 3C, addition of increasing concentrations of GSH (0.1-5 mM) to a buffered solution of FRET-MSNs induced a decrease in the green fluorescence (520 nm) accompanied by recovery of blue fluorescence (450 nm) upon excitation at 405 nm. This strongly indicated the cleavage of disulfide bond and the removal of the FRET acceptor, FITC-β-CD. Accordingly, the color of the solution changed from green to blue under UV lamp (365 nm) (FIG. 3A, inset). Fluorescence spectrum of the isolated nanoparticles after redispersing in PBS (pH 7.4) revealed that these nanoparticles only show the emission at 450 nm. Based on these results, we can confirm the redox-responsive behavior of our FRET-MSNs, which results in a concomitant change in the FRET signal.

Correlating Drug Release from FRET-MSNs to the FRET Signal.

Figure 4:
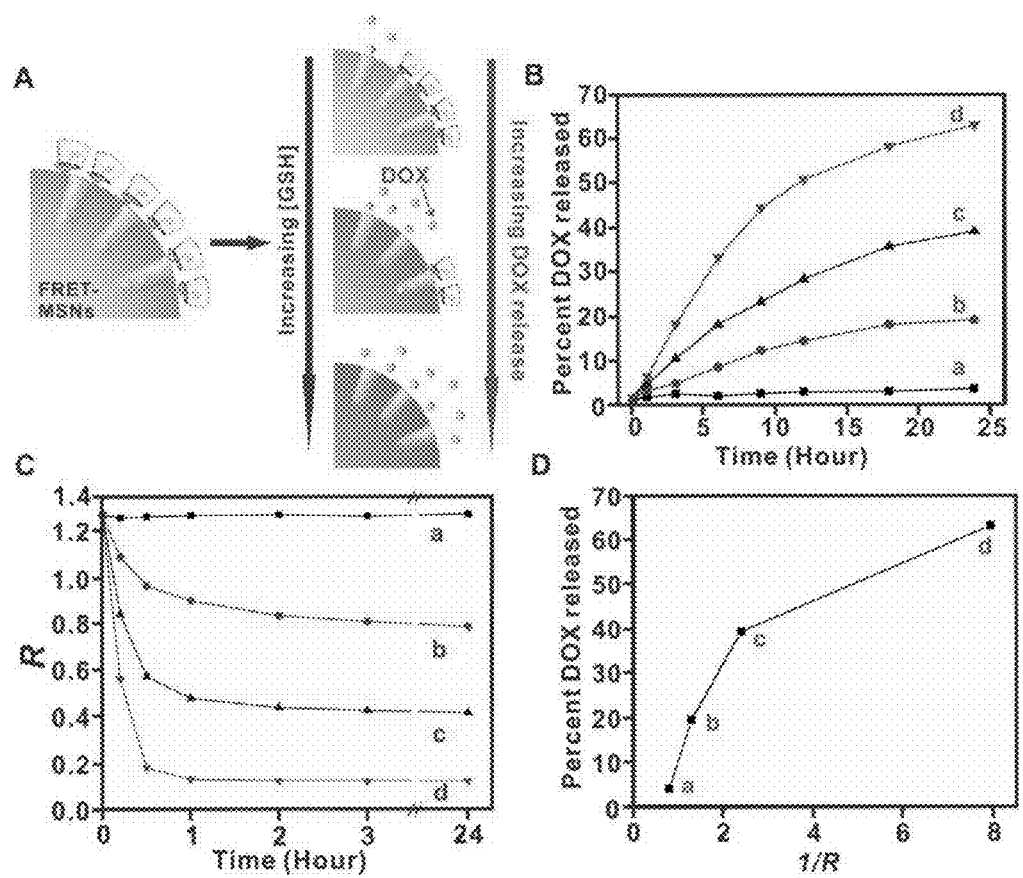
FIG. 4 depicts (A) Scheme showing the release of DOX at different concentrations of GSH and the corresponding change in FRET signal as well color of FRET-MSNs. (B) Percent DOX released from the FRET-MSNs at different time points following treatment with increasing concentrations of GSH. (C) Change in FRET signal R at different time points following treatment of FRET-MSNs with increasing concentrations of GSH. (D) Correlation between percent DOX released and change in FRET signal R (plotted as 1/R) at 24 h after GSH treatment. (a=no GSH, b=0.1 mM GSH, c=1 mM GSH and d=5 mM GSH)

Once we confirmed the redox-responsive gating behavior of our FRET-MSNs, our next step was to utilize their FRET properties for monitoring the drug release from the pores. Since the modulation of FRET is integrated within the uncapping event, we hypothesize that the corresponding change in the FRET signal can be utilized for monitoring the drug release on a temporal level (FIG. 4A). To demonstrate this, we chose doxorubicin (DOX) as our model cargo, which was loaded into the pores of MSNs by first mixing aqueous buffered solutions of CHC-MSNs and DOX for 12 h. Thereafter, the pores were capped with FITC-β-CD and the final product (DOX-loaded FRET-MSNs) was isolated by centrifugation after repeated washing. The amount of DOX loaded into the pores of FRET-MSNs was determined to be 41.3 mg DOX/g of FRET-MSNs.

The DOX-loaded FRET-MSNs were well-dispersed in aqueous solutions, owing to the presence of hydrophilic β-CD moieties on their surface, which can be exploited for the delivery of hydrophobic cargoes, like anti-cancer drugs. To investigate the capping efficiency, DOX loaded FRET-MSNs were dispersed in PBS (pH 7.4) and the absorbance of the released DOX in the absence of GSH was first monitored. As shown in FIG. 4B (curve a), negligible release of DOX was observed over a period of 24 h, indicating that the FRET-MSNs remain intact in the absence of GSH. In contrast, the release profiles of DOX in the presence of varying concentrations of GSH depict an increase in the percent DOX released as time progressed (FIG. 4B, curve b-d). From FIG. 4B, we can see that the percent DOX released from the FRET-MSNs was dependent on GSH concentration, wherein concentrations of 0.1 mM or higher lead to significantly faster and greater release of DOX.

Since the release of DOX only occurs when the pores are unlocked as a consequence of FITC-β-CD diffusing away from the FRET-MSNs, we also observed a corresponding change in the FRET signal R. As shown in FIG. 4C, addition of GSH (0.1 mM) to Dox-loaded FRET-MSNs induced a relatively slow time-dependent decrease in FRET signal over a period of 3 h, while higher concentrations of GSH lead to faster decrease in the FRET signal, reaching a minimal value of R within 1 h at 5 mM concentration of GSH. These GSH-concentration induced changes in FRET signal remained constant over a period of 24 h, at which the release of DOX also reached a plateau. From this data (t=24 h), a correlation between the amount of DOX released and FRET signal R was obtained (FIG. 4D), which strongly suggested that the FRET-MSNs have the capability of monitoring the drug release in real-time.

Observing FRET Change in Cancer Cells Using FRET-MSNs.

Prior to using the FRET-MSNs for cellular studies, we identified a range of concentrations within which the FRET-MSNs demonstrated minimal cytotoxicity. Using a cell proliferation assay, we found that concentrations lower than 20 μg/mL induced negligible cytotoxicity in HeLa cells and hence for all of our experiments, we utilized FRET-MSNs within this concentration range. To investigate the change in FRET signal following uptake and localization of FRET-MSNs in mammalian cells, we incubated the FRET-MSNs with cervical cancer cells (HeLa) and observed the change in FRET signal over extended periods of time (0 to 24 h) using confocal fluorescence microscopy.

Figure 5:
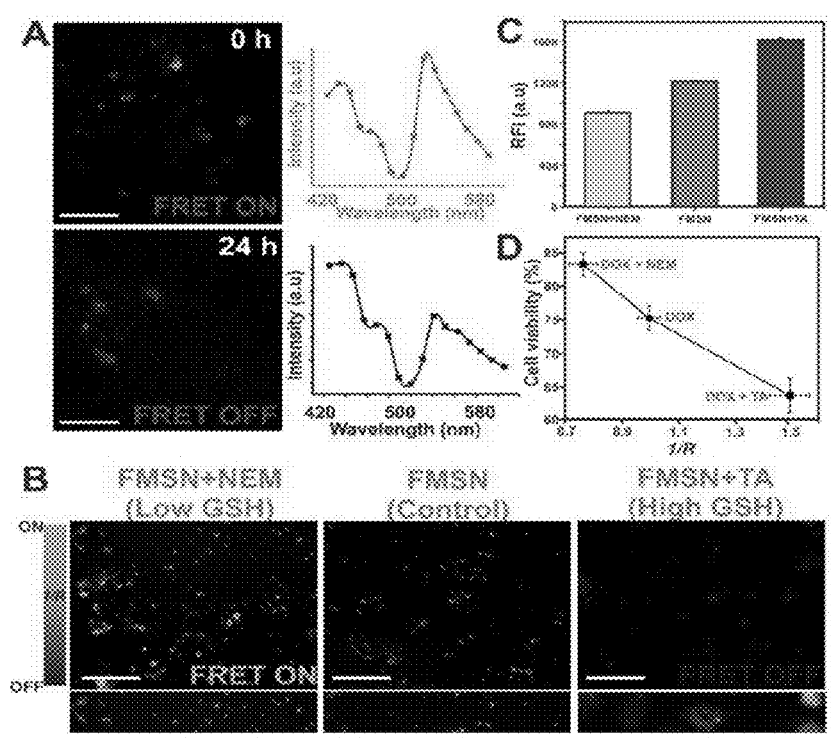
FIG. 5 depicts (A) Confocal microscopy images (Left panel) depicting the change in FRET signal in HeLa cells treated with FRET-MSNs at different time points. Right panel shows the corresponding change in the average fluorescence intensities, when the cells were excited with 405 nm light (more details see Figure S7). Scale bar is 1 µm, (B) Fluorescence microscopy images showing the change in the fluorescence intensity (FRET channel, 405 nm excitation, top panel, and the merged images with FITC channel which used 488 nm as excitation, bottom panel) upon varying intracellular GSH concentration of HeLa cells, prior to treatment with FRET-MSNs. Cells treated with N-ethyl maleimide (NEM, 5 µM) present low levels of GSH, thereby FRET signal is on; whereas, the cells treated with thiotic acid (TA, 10 µM) have increased GSH levels and hence the FRET is turned off. The bar (top left corner) indicates the correlation between FRET signal R and the color of the FRET-MSNs seen in the top panel. Scale bar is 5 µm (C) Quantitative comparison of the relative fluorescence intensities (RFI, Em=450 nm, Ex=405 nm), of the HeLa cells treated with TA and NEM. (D) Correlation between FRET signal R and cell viability, when the HeLa cells were treated with DOX loaded FRET-MSNs at varying GSH concentrations.

As seen in FIG. 5A (top left), at time t=0 h, blue-green spots were visible in the perinuclear region of HeLa cells when they were excited using 405 nm light, indicating intact FRET-MSNs with the FRET signal ON. From the emission spectrum (FIG. 5A, top right), we can see that these spots show lower blue emission, but stronger green emission thus confirming that most of the FRET-MSNs were in the "FRET ON" stage at this time-point. However, at approximately t=24 h, an increase in the blue fluorescence intensity and a corresponding decrease in the green fluorescence intensity (FIG. 5A, bottom left) were observed when the cells were excited using 405 nm light.

This was consistent with our expectation as the cleavage of disulfide bond would lead to the removal of FITC-β-CD cap, thereby leading to the recovery of the blue fluorescence intensity (FIG. 5A, bottom right). The removal of FITC-β-CD cap was further confirmed by observing diffuse FITC fluorescence throughout the cytoplasm, when the cells were excited using FITC channel (488 nm). These results demonstrated that we were able to monitor the change in the intracellular FRET signal over a period of time by using confocal microscopy.

As shown earlier, we have already demonstrated that our FRET-MSNs can respond to the presence of exogenous GSH by releasing the entrapped cargo with concurrent change in the FRET signal. However, in order to demonstrate this in mammalian cells, we used thioctic acid (TA, a GSH synthesis enhancer, 10 μM) and N-ethylmaleimide (NEM, a GSH scavenger, 5 μM) to modulate the intracellular GSH concentration. The HeLa cells were incubated with TA and NEM, 10 min prior to incubating with the FRET-MSNs and were subsequently analyzed using fluorescence microscopy.

As depicted in FIG. 5B, we observed a clear enhancement in the characteristic coumarin emission at 450 nm for the cells treated with TA in FRET channel (Ex=405 nm), coupled with increased FITC fluorescence in FITC channel (Ex=488 nm), indicating that higher number of the molecular valves (FITC-β-CD) were being removed from the surface of FRET-MSNs due to increased intracellular GSH concentration and were subsequently diffused into the cytoplasm. On the contrary, a distinct punctate blue-green fluorescence in FRET channel, indicating FRET ON, was seen in the perinuclear region in case of cells treated with NEM. Since NEM decreases intracellular GSH concentration, there will be negligible cleavage and subsequent release of FITC-β-CD, hence resulting in the FRET being ON.

As seen in FIG. 5C, quantitative analysis of the relative intensities of coumarin emission (Ex=405 nm. Em=450 nm) also showed a similar trend of increasing coumarin emission as the intracellular GSH concentration increased. Based on these results, we were also able to confirm that the release of the molecular gate (FITC-β-CD) occurred in response to the redox stimuli, GSH present in millimolar levels in the cytoplasm of cancer cells.

Monitoring Drug Release in Real-Time in Cancer Cells Using FRET-MSNs.

However, it is important to demonstrate if we can correlate this change in the FRET signal with the corresponding drug release and its downstream therapeutic efficacy. To prove this, we treated HeLa cells with TA and NEM to modulate the cytoplasmic GSH concentration prior to the addition of DOX-loaded FRET-MSNs, and the viability of HeLa cells was monitored 24 h after treatment. The change in intracellular GSH concentration will result in a change in the extent of disulfide bond cleavage, which shall be displayed as a change in the FRET signal R as well as the amount of DOX released.

Since the amount of DOX released from the nanoparticles influences the viability of cells, we can then correlate the change in FRET signal with the cell viability. As expected, the presence of TA, which increased the intracellular GSH concentration, led to an increase in the unlocking of pores which was associated with a decrease in the cell viability as well as an decrease in the FRET signal, R (thus 1/R increases as seen in FIG. 5D, FRET OFF). In contrast, when the cells were pre-treated with the GSH scavenger, NEM, we observed an increase in the cell viability as well as a increase in the FRET signal ratio, R (thus 1/R decreases as seen in FIG. 5D, FRET ON). These results demonstrated the ability of our proposed FRET-MSNs based DDS in real-time monitoring drug release and reporting cell viability.

Accordingly, we have successfully demonstrated the formation of redox-responsive fluorescent MSNs, comprised of an integrated FRET-based real-time monitoring system, which enabled tracking the release of the payload from the pores of the MSNs in real-time, by measuring the change in the FRET signal. We have shown a good correlation between the change in the FRET signal and the extent of drug released at different GSH concentrations both at the solution level as well as inside the cells. The advantage of our platform is that it can be extended to any cargo, fluorescent or non-fluorescent, as the molecular structures responsible for real-time monitoring are integrated within the unlocking mechanism present on the nanoparticle, and hence, we do not need to rely on the optical properties of the drug or a model dye.

As such, we can monitor the release of the cargo on a temporal level, even if the drug is non-fluorescent, thus demonstrating the versatility of our platform. Additionally, no structural modification of the drug is required as the donor-acceptor pair is integrated within the nanoparticles, thereby preserving the drug efficacy. Numerous studies have demonstrated significantly higher intracellular glutathione concentrations in cancer cells as compared to normal cells, we can expect our FRET-MSNs to release the biomolecules more selectively in cancer cells. However, we expect the application of the FRET-MSNs to extend to any trigger such as pH or temperature by making appropriate structural modifications, since the FRET signal only depends on the donor-acceptor pair.

EXAMPLES

Materials

N-Boc-Cysteine, 2,2'-Dithiodipyridine, 1-Adamantanethiol, 7-Hydroxycoumarin-3-carboxylic acid, 1-Ethyl-3-(3-dimethylaminopropyl)carbodiimide hydrochloride (ED-C.HCl), N-Hydroxysuccinimide, triethoxysilane (TEOS), (3-Aminopropyl)triethoxysilane (APTES), β-Cyclodextrine (β-CD), Fluorescein isothiocyanate (FITC), 4-Dimethylaminopyridine (DMAP) were purchased from Sigma-Aldrich or TCI Chemical and used as received.

Methods

UV-vis absorption spectra were recorded on a Varian Cary 50 spectrophotometer. Fluorescence spectra were recorder on a Varian Cary Eclipse fluorescence spectrophotometer. FT-IR spectra were collected on an Avatar Nicolet FT-IR330 spectrometer. Raman spectrum characterizations were performed on Laser Raman, Renishaw inVia Raman microscope. $^1$H NMR was acquired on Varian 400 MHz NMR spectrometer. ESI-MS was collected on Finnigan LCQ™ DUO LC/MS spectrometer. Transmission electron microscopy (TEM) was performed on a Topcon 002B electron microscope at 200 kV. Sample preparation was carried out by placing a drop of the freshly prepared colloidal solution on a carbon-coated copper grid and allowing the solution to evaporate. Nitrogen adsorption-desorption measurements were performed on a Micromeritics Tristar-3000 surface area analyzer at −196° C. The sample was dried at 200° C. for 3 h before analysis. The Burnauer-Emmett-Teller (BET) specific surface areas were calculated using the first 10 experimental data points. Pore volumes were determined from the amount of $N_2$ adsorbed at the single point $P/P_0$=0.98.

Synthesis of FRET-MSNs (a) $NH_2$-MSNs: In a typical synthesis procedure, 28 mg of sodium hydroxide and 100 mg of cetyl trimethylammonium bromide (CTAB) in sequence were completely dissolved into 50 mL of deionized water under vigorous stirring at 80° C. After the solution became clear, 0.5 mL of TEOS was added dropwise in 10 min. After 3 hours, 20 μl of APTES was added and the vigorous stirring was continued for 20 h, and then milk-white as-synthesized materials were collected by centrifugation. In order to remove the surfactant, the as-synthesized materials were refluxed in a solution consisting of 50 mL ethanol and 0.5 mL hydrochloric acid (36-38%) for 12 hours, centrifuged and finally washed several times with methanol. The final products were dried for 12 h at 120° C. in vacuum.

(b) Cys-MSNs: To a solution of N-Boc-cysteine (22 mg) and N-hydroxysuccinimide (NHS, 25 mg) in 5 mL anhydrous DMF at 0° C., 1-ethyl-3-(3-dimethylaminopropyl)carbodiimide hydrochloride (EDC.HCl, 31 mg) was added. The solution was stirred at 0° C. for 30 min and recovered to room temperature for additional 4 hours. Then 100 mg of $NH_2$-MSNs in 5 mL DMF solution was added slowly and the mixture was keep stirring overnight under $N_2$. The nanoparticles were collected by centrifugation and washed several times with DMF and methanol, and finally dried in vacuum to obtain Cys-MSNs.

(c) Cys-TA-MSNs: A solution of Cys-MSNs (80 mg) in 5 mL methanol was added dropwise into a solution of 2,2'-dithiodipyridine (0.1 g) in methanol/pH7.4 PBS solution (v/v, 10 mL/1.5 mL). The mixture was stirred at room temperature overnight and the nanoparticles were collected by centrifugation, washed thrice with methanol and finally redispersed in 10 mL methanol. 1-adamantanethiol (0.1 g) in 2 mL methanol was then added to the above solution and the mixture was stirred overnight at room temperature under $N_2$ atmosphere. The Cys-TA-MSNs were collected by centrifugation, washed several times with methanol, and then dried under vacuum.

(d) CHC-MSNs: 5 mL DCM solution of Cys-TA-MSNs (60 mg) was cooled to 0° C. for 30 min and then 2 mL trifluoroacetic acid (TFA) were added. The mixture was stirred at 0° C. for 30 min and then recovered to room temperature for an additional 3 hours. Then 10 mL of methanol was added to dilute the mixture. The nanoparticles were collected by centrifugation and washed several times with methanol, dried in vacuum, and finally redispersed in 5 mL anhydrous DMF. To a solution of 7-hydroxycoumarin-3-carboxylic acid (100 mg) and NHS (80 mg) in 5 mL anhydrous DMF at 0° C., 70 mg of EDC.HCl were added. The solution was stirred at 0° C. for 30 min and recovered to room temperature for an additional 4 hours. Then, the 5 mL of DMF solution consisting of CHC-MSN nanoparticles was added slowly to the solution and the mixture was keep for stirring overnight. The nanoparticles were collected by centrifugation and washed several times with DMF and methanol, and then finally dried in vacuum to obtain the CHC-MSNs.

Synthesis of FITC-β-CD: Mono-6-deoxy-6-amino-β-cyclodextrin ($NH_2$-β-CD) was first synthesized by a previously reported method.[57] $^1$H NMR (300 MHz, $D_2O$): δ 4.97 (s, 7H), 3.74-3.88 (m), 3.38-3.56 (m), 3.08 (d, 1H, J=14.2 Hz), 2.84 (dd, 1H, J1=7.0 Hz, J2=14.1 Hz). ESI-MS m/z 1132.3 [M-H]$^-$. 38 mg FITC, 10 mg DMAP and 0.1 g $NH_2$-β-CD were added into 5 mL anhydrous DMF and the solution was stirred overnight at room temperature under $N_2$. 10 mL acetone was added to the solution and the precipitate was collected and washed with acetone several times. ESI-MS m/z 1521.9 [M-H]$^-$, 761.3 [M-2H]/2$^-$.

Characterizations: UV-vis absorption spectra were recorded on a Varian Cary 50 spectrophotometer. Fluorescence spectra were recorded on a Varian Cary Eclipse fluorescence spectrophotometer. FT-IR spectra were collected on an Avatar Nicolet FT-IR330 spectrometer. Raman spectrum characterizations were performed on Laser Raman, Renishaw inVia Raman microscope. $^1$H NMR was acquired on Varian 400 MHz NMR spectrometer. ESI-MS was collected on Finnigan LCQ™ DUO LC/MS spectrometer. Transmission electron microscopy (TEM) was performed on a Topcon 002B electron microscope at 200 kV. Sample preparation was carried out by placing a drop of the freshly prepared colloidal solution on a carbon-coated copper grid and allowing the solution to evaporate. Nitrogen adsorption-desorption measurements were performed on a Micromeritics Tristar-3000 surface area analyzer at −196° C. The sample was dried at 200° C. for 3 h before analysis. The Burnauer-Emmett-Teller (BET) specific surface areas were calculated using the first 10 experimental data points. Pore volumes were determined from the amount of $N_2$ adsorbed at the single point, $P/P_0$=0.98.

Cell-lines and culture: HeLa cells were used for FRET-MSNs. HeLa cells were cultured in DMEM supplemented with 10% FBS and 1% streptomycin-penicillin. For the delivery experiment, passaged cells were prepared to 40-60% confluency in 24-well plates. After 24 h of plating, media was exchanged with serum-free basal media (500 µL) and FRET-MSNs/X-tremeGENE complexes (50 µL) were added. After incubation for 6 hours, media was exchanged with normal growth medium. Fluorescence measurements were performed after 0-24 h after transfection.

Imaging of FRET-MSNs: At different time points following transfection, the cells were imaged using fluorescent microscopy. The effect of GSH concentration on the FRET signal was studied using the eplifluorescence microscopy. For this purpose, the fluorescent and phase contrast images were obtained using the Nikon T2500 inverted epifluorescence microscope. Each image was captured with different channels and focus. Images were processed and overlapped using Image-Pro (Media Cybernetics) and ImageJ (NIH). In order to monitor and quantify the change in FRET signal in vitro, confocal imaging was done using Zeiss LSM 510-META confocal microscope equipped with an Axiovert 200 inverted Scope.

What is claimed is:

1. A complex comprising: (a) a drug carrier comprising coumarin-labeled-cysteine tethered mesoporous silica nanoparticles (MSNs) loaded with a pharmaceutically active agent, said cysteine tethered MSNs comprising a cleavable disulfide linkage; and (b) a fluorescein isothiocyanate-β-cyclodextrin (FITC-β-CD) positioned in proximity to said cysteine tethered MSNs to form a complex, said complex having an emission wavelength different from the emission wavelength of said cysteine tethered MSNs after cleavage of the disulfide linkage.

2. The complex of claim 1, wherein said cysteine tethered MSNs comprise an adamantine moiety.

3. The complex of claim 2, wherein said cysteine tethered MSNs are complexed to said FITC-β-CD via the interaction between said adamantine moiety and the cyclodextrin of said FITC-β-CD.

4. The complex of claim 1, wherein said FITC-β-CD is derived from FITC and Mono-6-deoxy-6-amino-β-cyclodextrin.

5. The complex of claim 1, wherein said disulfide linkage is cleavable by a reducing agent.

6. The complex of claim 5, wherein said reducing agent is glutathione.

7. The complex of claim 1, where the complex has an emission wavelength at 520 nm.

8. The complex of claim 1, wherein the complex has dual emission wavelengths at 450 nm and 520 nm when excited at 405 nm.

9. The complex of claim 1, wherein said wavelength of said cysteine tethered MSNs after the cleavage of said disulfide linkage is in the range of 430-480 nm.

10. The complex of claim 1, wherein said pharmaceutically active agent is doxorubicin (DOX).

11. A method of monitoring the release of a pharmaceutically active agent or cell viability comprising contacting the complex of claim 1 with cancer cells and detecting the change in wavelength or intensity of the emission spectrum.

12. The method of claim 11, wherein the complex is excited at 405 nm.

13. The method of claim 11, wherein an increase in intensity at 450 nm indicates the release of the pharmaceutically active agent.

14. A method of producing a complex of claim 1, comprising mixing (a) coumarin-labeled-cysteine tethered mesoporous silica nanoparticles (MSNs) loaded with a pharmaceutically active agent, said cysteine tethered MSNs comprising a cleavable disulfide linkage; and (b) a fluorescein isothiocyanate-β-cyclodextrin (FITC-β-CD).

15. The complex of claim 1, wherein said coumarin-labeled-cysteine is 3-carboxy-7-hydroxyl-coumarin (CHC)-labeled-cysteine.

* * * * *